United States Patent [19]

Burton et al.

[11] Patent Number: 4,910,324

[45] Date of Patent: Mar. 20, 1990

[54] METHOD OF TRANSHALOGENATING A HALOPHOSPHORUS COMPOUND WITH FLUORIDE

[75] Inventors: Lester P. J. Burton; Vincent J. Gatto, both of Baton Rouge, La.

[73] Assignee: Ethyl Corporation, Richmond, Va.

[21] Appl. No.: 237,095

[22] Filed: Aug. 29, 1988

[51] Int. Cl.$^4$ ............................................. C07F 9/14
[52] U.S. Cl. ...................................... 558/84; 558/140
[58] Field of Search ................................. 558/84, 140

[56] References Cited

PUBLICATIONS

Kosolapoff et al., "Organic Phosphorus Compounds", vol. 6, (1974), pp. 319–321.

Primary Examiner—Anton H. Sutto
Attorney, Agent, or Firm—Joseph D. Odenweller; W. G. Montgomery

[57] ABSTRACT

Phosphorus compounds having at least one chlorine, bromine or iodine bonded directly to phosphorus are transhalogenated with fluorine by reaction with a fluoride salt, e.g., KF, or ammonium fluoride in an inert solvent in the presence of a catalytic amount of a carboxylic acid.

28 Claims, No Drawings

METHOD OF TRANSHALOGENATING A HALOPHOSPHORUS COMPOUND WITH FLUORIDE

BACKGROUND

It is known that fluorine can be exchanged for chlorine, bromine or iodine bonded to phosphorus by reaction of the halophosphorus compound with a metal fluoride. The transhalogenation reaction is quite slow and difficult to push to completion. It is sometimes desirable to replace chlorine, bromine, or iodine bonded to phosphorus with a fluorine atom. For example, Burton U. S. Serial No. 020,023 filed Feb. 27, 1987 describes a family of hydrocarbyl fluorophosphites that are very effective stabilizers in polyolefins, especially in combination with phenolic antioxidants, and are also hydrolytically stable. These compounds are made by first forming a hydrocarbyl chlorophosphite by reaction of an appropriate aliphatic or aromatic hydroxy compound with $PCl_3$ to form a mono or dichlorophosphite and then transhalogenating the chlorine atom with fluorine by reaction with a metal fluoride such as potassium fluoride.

L. P. J. Burton and M. S. Ao, in U.S. Serial No. 110,198 filed Oct. 19, 1987, disclose that the transhalogenation of a chlorine, bromine or iodine atom bonded directly to phosphorus by reaction with a fluoride salt can be sharply promoted by including in the reaction mixture a hydrogen halide salt of a pyridine-type compound such as pyridine hydrochloride. While this constitutes an important contribution to the art by decreasing the amount of time required to complete the transhalogenation reaction, it is necessary to remove the promotor from the product of reaction at the completion of the reaction by introducing ammonia into the reaction mixture to convert the pyridine hydrochloride catalyst to ammonium chloride and separate it from the reaction mixture as a precipitate. At the plant-size scale, this is a difficult and expensive procedure and also creates a waste disposal problem since the precipitate typically contains solvent used in the process which must be removed from the filter cake before disposal. Further, pyridine is freed from the catalytic complex by the introduction of ammonia into the reaction mixture which must be separated from the reaction product by distillation and recycled for reuse. This also adds to the cost of production. Also, the pyridine-HCl complex is corrosive of the metal equipment in which the product is made.

In pending application Serial No. 227,231 filed by K. A. Keblys, M. S. Ao and L. P. J. Burton there is disclosed a method for exchanging a halogen bonded to a phosphorus atom with fluorine by reacting a phosphorus compound having a halogen selected from chlorine, bromine or iodine bonded directly to phosphorus with a hydrogen fluoride salt of a pyridine-type compound such as pyridine hydrofluoride in an inert solvent. This method also constitutes an important contribution to the art by providing for shortened transhalogenation reaction times and avoiding the use of expensive metal fluoride reactants such as potassium fluoride inherent in the practice of the process disclosed in aforediscussed application Serial No. 110,198. However, a disadvantage of this method is that pyridine hydrochloride is formed as a by-product from the reaction of a portion of th pyridine hydrofluoride with the halophosphorus starting material, which, as previously discussed, requires removal from the product of reaction at the completion of the reaction by introducing ammonia into the reaction mixture to convert the pyridine-hydrochloride to ammonium chloride and thereafter separating it from the reaction mixture as a precipitate, which, as noted previously, results in economic penalties. Thus, a need exists for an improved method.

SUMMARY OF THE INVENTION

It has now been discovered that the transhalogenation of phosphorus compounds having at least one chlorine, bromine or iodine bonded directly to phosphorus by reaction with a flouride salt can be sharply promoted by including in the reaction mixture a catalytic or promoter amount of a carboxylic acid thereby avoiding, the problems inherent in the use or formation of pyridine-hydrochloride in the transhalogenation reaction.

DESCRIPTION OF THE PREFERRED EMBODIMENTS

Accordingly, a preferred embodiment of the invention is a process for exchanging a halogen bonded to a phosphorus atom with fluorine said process comprising reacting a phosphorus compound having a halogen selected from chlorine, bromine or iodine bonded directly to phosphorus with a fluoride salt in an inert solvent in the presence of a catalytic amount of a carboxylic acid.

The phosphorus bound halogen that is exchanged with fluorine can be chlorine, bromine or iodine. The exchange is more difficult with chlorine but phosphorus bound chlorine compounds are the most readily available. Accordingly the preferred phosphorus bound halogen is chlorine.

The fluoride salt can be any metal fluoride capable of transhalogenating phosphorus bound chlorine, bromine or iodine. These include $LiF$, $NaF$, $KF$, $RbF$, $CaF_2$, $CsF$, $SbF_3$, $KHF_2$, $AgF$, $HgF_2$, $CoF_3$, $SnF_4$ and the like. Likewise other fluoride salts such as an ammonium fluoride can be used. The more preferred fluorides are the alkali metal fluorides such as $NaF$ and especially $KF$.

The amount of fluoride salt should be at least a stoichiometric amount. In general, use of about 1–10 equivalents of fluoride per equivalent of phosphorus bound halogen is recommended. More preferably, the amount of fluoride is about 1–5 equivalents and most preferably 1.1–2 equivalents per equivalent of phosphorus bound halogen.

The fluoride salt should be in finely divided form to present a high surface area since the reaction is heterogeneous. Ground, milled or spray dried metal fluoride is most useful.

The process can be conducted in a number of inert solvents. Inert solvents include aliphatic hydrocarbons such as hexane, heptane, octane, cyclohexane, and the like including mixtures thereof.

The more preferred inert solvents are the aromatic solvents which boil in the range of about 80–176° C. These include benzene, toluene, xylene and mesitylene including all isomers and all mixtures of isomers and solvents.

Halogenated solvents such as carbon tetrachloride, 1,2-dichloroethane, methylenebromide, 1,1,2-trichloroethane, chlorobenzene, dichlorobenzene and the like can be used as solvents.

The amount of solvent is not critical. A useful amount is about 50–500 parts by weight solvent per 100 parts of phosphorus compound.

The transhalogenation should be conducted at a temperature high enough to cause the halogen exchange to proceed but not so high as to cause undesired degradation of the reaction products. A useful temperature range is about 20–300° C. more preferably about 50–200° C. and most preferably at the atmospheric pressure reflux temperature of the reaction mixture. Higher temperatures will of course require a sealed system under pressure.

The reaction time should be long enough to complete the reaction. The reaction time is much shorter than the time required to conduct the transhalogenation without the use of the carboxylic acid promoter. The reaction is generally complete in 0.5–12 hours and in most case in approximately 1–2 hours.

The promoter is any carboxylic acid that will promote or cause the transhalogenation reaction to proceed at a higher rate. Examples include monocarboxylic acids such as formic acid, acetic acid, propionic acid, valeric acid, caproic acid, octanoic acid, acrylic acid, methacrylic acid, crotonic acid, benzoic acid, toluic acid, phenylacetic acid, trifluoroacetic acid and the like; dicarboxylic acids such as oxalic acid, malonic acid, succinic acid, glutamic acid, adipic acid, maleic acid, fumaric acid, phthalic acid, isophthalic acid, terephthalic acid and the like; and tricarboxylic acids such as citric acid, aconitic acid, trimellitic acid and the like. In addition to the above, oxycarboxylic acids such as glycolic acid, tartaric acid, malic acid, lactic acid, salicylic acid, mandelic acid and the like and ketocarboxylic acids such as acetoacetic acid and the like can be used. Of these, those acids having 7 or fewer carbon atoms are preferred. Acetic acid is the most preferred carboxylic acid promoter.

The amount of promoter should be at least a promoter amount, that is an amount that causes the transhalogenation to proceed at a higher rate. A useful range is about 1.0–500 parts by weight promoter per 100 parts of phosphorus compound. A preferred amount is about 5.0–300 parts promoter and more preferably about 10–200 parts promoter per 100 parts phosphorus compound.

The phosphorus compounds having chlorine, bromine or iodine bonded to phosphorus can have one or two of such halogens bonded to phosphorus. The remaining group or groups bonded to phosphorus are substituted or unsubstituted hydrocarbyl, hydrocarbyloxy or hydrocarbylthio groups. Examples of such halophosphorus compounds are methyl dichlorophosphite, ethyl dichlorophosphite, butyl dichlorophosphite, dodecyl dichlorothiophosphite, eicosyl dichlorophosphite, triacontyl dichlorophosphite, methyl dibromophosphite, propyl dibromophosphite, tetradecyl diiodophosphite, eicosyl chlorobromophosphite, triacontyl bromoiodophosphite, methyl dichlorophosphate, 0-ethyl dichlorothiophosphate, decyl dichlorophosphate, eicosyl dichlorophosphate, 0-triacontyl dichlorothiophosphate, methyl dibromophosphate, octyl dibromophosphate, octadecyl dibromothiophosphate, triacontyl dibromophosphate, methyl diiodophosphate, hexadecyl diiodophosphate, eicosyl chloroiodophosphate, 0-methyl dichlorothiophosphate, 0-decyl dibromothiophosphate, eicosyl diiododithiophosphate, triacontyl dichlorothiophosphonate, phenyl dichlorophosphite, phenyl dibromophosphite, phenyl diiodophosphite, benzyl dichlorophosphite, benzyl dibromophosphite, methyldichlorophosphine, butyldichlorophosphine, dodecyldichlorophosphine, eicosyldibromophosphine, triacontyldiiodophosphine, cyclohexyl dichlorophosphite, cyclohexyl dibromophosphite, cyclohexyl dichlorothiophosphite, cyclohexyl dibromodithiophosphate, dimethyl chlorophosphite, didodecyl chlorophosphite, dieicosyl bromophosphite, ditriacontyl iodophosphite, dimethylchlorophosphine, didodecyliodophosphine, dimethyl chlorothiophosphite, dieicosyl bromodithiophosphite, dimethyl chlorophosphate, didodecyl bromophosphate, dieicosyl bromophosphate, diphenyl chlorophosphite, diphenyl bromophosphite, diphenyl chlorophosphate, diphenyl bromotrithiophosphate, diphenyl chlorophosphate, dibenzyl chlorophosphate, dibenzyl bromophosphite, diphenyl chlorotrithiophosphate, dicyclohexyl chlorophosphate, phenyldichlorophosphine, diphenylbromophosphine, dibenzylchlorophosphine, dimethylchlorophosphine, didodecyl bromophosphine, methyleicosyliodophosphine, benzyldibromophosphine and the like.

The preferred phosphorus compounds have the structure

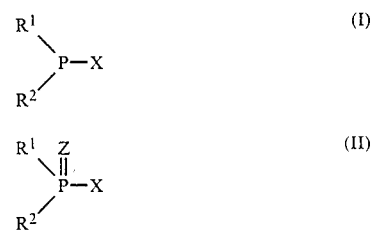

wherein X is chlorine, bromine or iodine, Z is oxygen or sulphur, $R^1$ is selected from the group consisting of substituted and unsubstituted alkoxy, thioalkoxy, aryloxy, thioaryloxy, cycloalkoxy, alkenoxy, and arylalkoxy and $R^2$ is selected from the same group as $R^1$ or is X or $R^1$ and $R^2$ can jointly form a substituted or unsubstituted divalent hydrocarbon group bonded at each end through oxygen or sulphur to the phosphorus atom in structure I or II. More preferably $R^2$ is not X.

Examples of the preferred starting phosphorus compounds are dimethyl chlorophosphite, diethyl chlorophosphite, diethyl bromophosphite, dibutyl iodophosphite, dioctyl chlorophosphite, didodecyl bromophosphite, dieicosyl iodophosphite, triacontyl dichlorophosphite, butyl dibromophosphite, methyl dodecyl chlorophosphite, eicosyl dichlorophosphite, triacontyl dibromophosphite, dimethyl chlorothiophosphite, dodecyl dibromothiophosphite, dioctadecyl chlorothiophosphite, phenyl dichlorophosphite, diphenyl bromophosphite, di(4-tert-butylphenyl) chlorophosphite, di(2,4-di-tert-butylphenyl) bromophosphite, 2-isopropyl-4-methylphenyl dichlorophosphite, di(4-tert-hexylphenyl) chlorophosphite, diphenyl chlorothiophosphite, phenyl dibromothiophosphite, 1-naphthyl dichlorophosphite, dicyclohexyl chlorophosphite, dicyclooctyl bromophosphite, cyclododecyl dichlorophosphite, dicyclohexyl bromothiophosphite, diallyl iodophosphite, di-(but-2-enyl) chlorophosphite benzyl dichlorophosphite, dibenzyl bromophosphite, di(alpha-methylbenzyl) chlorophosphite, ethyleneglycol chlorophosphite, 2,2'-methylenebis(4,6-di-tertbutylphenyl) chlorophosphite, 2,2'-methylenebis(4-methyl6-tert-butylphenyl) bromophosphite, 2,2'-bis(4,6-di-tert-butylphenyl) chlorophosphite, 2,2'-bis(4,6-di-tert-butylphenyl) chlorophosphate, 2,2'-ethylidenebis(4,6-di-tert-butylphenyl) chlorophosphite, 2,2'-ethylidenebis(4,6-di-tert-butylphenyl) chlorophosphate, di(2,4-di-tert-butylphenyl) chlorophosphate, di(2,6-di-tert-butylphenyl) chlorophosphite, 2,4-di-tert-butylphenyl dichlorodithiophosphate, di[4-(octadecyloxycarbonylethyl)-2,6-tert-butylphenyl]-chlorophosphite and the like.

In the more preferred phosphorus compounds $R^1$ and $R^2$ jointly form a divalent hydrocarbon group having the structure

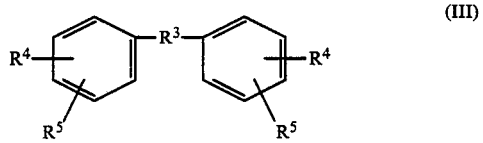

(III)

wherein $R^3$ is a methylene or alkylidene bridge or is absent forming a direct ortho-ortho bond between the benzene rings, $R^4$ and $R^5$ are independently selected from alkyl groups, cycloalkyl groups and aralkyl groups and the unsubstituted bond on each benzene ring is bonded through oxygen to said phosphorus atom in structures I or II.

Examples of phosphorus compounds which contain the above divalent hydrocarbon group are 2,2'-methylenebis(4-methyl-6-tert butylphenyl) chlorophosphite, 2,2'-methylenebis(4-methyl-6-tertbutylphenyl) chlorophosphate, 2,2'-methylenebis(4,6-di-tert-butylphenyl) bromophosphite, 2,2'-ethylidenebis(4-methyl-6-tert-butylphenyl) chlorophosphite, 2,2'-ethylidenebis(4-methyl-6-tert-butylphenyl) chlorophosphate, 2,2'-isopropylidenebis(4-methyl-6-tertpentylphenyl) bromophosphite, 2,2'-(butylidenebis(4,6-di-tert-butylphenyl) chlorophosphite, 2,2'-bis(4-sec-dodecyl-6-tert-butylphenyl) chlorophosphate, 2,2'-bis(4-methyl-6-tert-hexylphenyl) bromophosphite, 2,2'-bis(4-methyl-6-cyclohexylphenyl) chlorophosphate, 2,2'-ethylidenebis(4,6-dicyclohexylphenyl) chlorophosphite, 2,2'-methylenebis[4,6-di(alpha-methylbenzyl)-phenyl]bromothiophosphate, 2,2'-ethylidenebis(4-methyl-6(alpha-methylbenzyl)phenyl) chlorophosphite, 2,2'-bis[4,6-di(alpha-methylbenzyl)phenyl]bromophosphite and the like.

In a highly preferred embodiment the $R^4$ groups are bonded at the 6,6'-positions and the $R^5$ groups are bonded at the 4,4'-positions in structure III. Still more preferably both $R^4$ groups are tert-alkyls having 4–12 carbon atoms and $R^5$ is $C_{1-12}$ alkyl, especially a tert-alkyl of 4–12 carbon atoms.

The most preferred phosphorus compound used as a starting material is 2,2'-ethylidenebis(4,6-di-tert-butylphenyl) chlorophosphite.

The reaction is readily carried out by placing the finely divided fluoride salt and a solvent in a stirred reaction vessel together with the carboxylic acid promoter, heating to reaction temperature and adding the phosphorus compound to the vessel. This mixture is stirred at reaction temperature until the transhalogenation is substantially complete. The product can be recovered by conventional means such as by filtering to remove insoluble inorganic salts and then water-washing to remove residual salts and promoter. Product will usually crystallize on cooling or part of the solvent can then be removed by evaporation under vacuum followed by crystallization. Further purification of the remaining product can be achieved by conventional recrystallization.

The following examples show how the reaction is conducted.

EXAMPLE 1

The 2,2'-ethylidenebis(4,6-di-tert-butylphenyl) chlorophosphite starting material was made by heating mixture of 1300 grams of 2,2'-ethylidenebis(4,6-di-tert-butylphenol), 2 liters of xylene and 13 grams of pyridine in a reaction vessel to 100° C. while maintaining a nitrogen sweep over the reaction surface to assist in HCl removal and thereafter slowly adding 500 grams of $PCl_3$ to the reaction mixture over a period of 45 minutes. The mixture was then stirred and heated to 135° C. Stirring was continued for 1.5 hours at 135° C. under nitrogen and then allowed to cool to 10° C. The resultant solid was collected by filtration and 500 grams of the filter cake (1484 grams total weight) was washed with 500 grams of xylene and dried at about 80.C under vacuum overnight. Conversion to 2,2'-ethylidenebis(4,6-di-tertbutylphenyl) chlorophosphite was essentially complete. Analysis by GC (gas chromatography) showed 98 area percent 2,2'-ethylidenebis(4,6-di-tert-butylphenyl) chlorophosphite and 2.0 percent 2,2'-ethylenebis(4,6-di-tert- butylphenyl) hydrogenphosphonate.

A glass reaction vessel was charged with 1.3 grams (22.4 mmoles) of KF, 10 milliliters of toluene, and 1.2 milliliters (20.3 mmoles) of acetic acid. The mixture was vigorously stirred under a dry nitrogen atmosphere and slowly heated. At 80° C. 9.9 grams (20.3 mmoles) of the 2,2'-ethylidenebis(4,6-di-tertbutylphenyl) chlorophosphite starting material prepared as described in the preceding paragraph dissolved in 20 milliliters of hot toluene was added to the vessel over a 45 minute period. The reaction mixture was analyzed periodically by gas chromatography (GC area percent). The following table shows the compositions excluding solvent, acid, and salts.

| | Composition (GC Area Percent) | | | |
|---|---|---|---|---|
| Reaction Time (hrs) | Bisphenol[1] | Chloro-phosphite[2] | Fluoro-phosphite | Hydrogen-Phosphonate[3]/Other |
| 0.25 | 1.1 | 0 | 97.6 | 1.3 |
| 1.0 | 1.9 | 0 | 97.3 | 0.8 |
| 2.0 | 2.5 | 0 | 97.2 | 0.4 |
| 3.5 | 2.4 | 0 | 97.4 | 0.1 |

[1]2,2'-ethylidenebis(4,6-di-tert-butylphenol). (4,6-di-tert-butylphenol).
[2]2,2'-ethylidenebis(4,6-di-tert-butylphenyl) (4,6-di-tert-butylphenyl) chlorophosphite.
[3]2,2'-ethylidenebis(4,6-di-tert-butylphenyl) (4,6-di-tert-butylphenyl) hydrogenphosphonate.

The reaction was essentially complete in 15 minutes. The mixture was then poured into a stirred solution containing 20 grams of water and 2.6 grams of sodium bicarbonate maintained at 65° C. The phases were separated and the organic phase was washed with four 20 gram portions of water maintained at 65° C. The following table shows the composition after the aqueous washes.

| | Composition (GC Area Percent) | | | |
|---|---|---|---|---|
| Reaction Time (hrs) | Bisphenol | Chloro- phosphite | Fluoro- phosphite | Hydrogen- Phosphonate/ Other |
| After aqueous bicarbonate wash | 2.8 | 0 | 96.9 | 0.3 |
| After wash washes | 2.9 | 0 | 96.7 | 0.4 |

Excluding solvent, the final product contained 96.7% fluorophosphite.

EXAMPLE 2

A glass reaction vessel was charged with 1.3 grams (22.4 mmoles) of KF, 20 milliliters of toluene, and 9.9 grams (20.3 mmoles) of the 2,2'-ethylidenebis(4,6-di-tert-butylphenyl) chlorophosphite starting material prepared from Example 1. The mixture was vigorously stirred under a dry nitrogen atmosphere and slowly heated. At 80° C., 1.2 milliliters (20.3 mmoles) of acetic acid was added to the reaction vessel. The reaction mixture was analyzed periodically by gas chromatography (GC area percent). The following table shows the composition excluding solvent, acid and salts.

| | Composition (GC Area Percent) | | | |
|---|---|---|---|---|
| Reaction Time (hrs) | Bisphenol | Chloro- phosphite | Fluoro- phosphite | Hydrogen- Phosphonate/ Other |
| 0.25 | 6.2 | 0 | 88.4 | 5.5 |
| 2.0 | 6.0 | 0 | 91.9 | 2.2 |

Excluding solvent, acid, and salts, the final product contained 91.9% fluorophosphite.

EXAMPLE 3

A glass reaction vessel was charged with 1.3 grams (22.4 mmoles) of KF, 10 milliliters of toluene, and 2.1 grams (20.3 mmoles) of pivalic acid. The mixture was stirred vigorously under a dry nitrogen atmosphere and slowly heated. At 80° C, 9.9 grams (20.3 mmoles) of the 2,2'-ethylidenebis(4,6-di-tertbutylphenyl) chlorophosphite starting material prepared in Example 1 dissolved in 20 milliliters of hot toluene was added to the reaction vessel over a 45 minute period. The reaction mixture was analyzed periodically by gas chromatography. The following table shows the compositions excluding solvent, acid, and salts.

| | Composition (GC Area Percent) | | | |
|---|---|---|---|---|
| Reaction Time (hrs) | Bisphenol | Chloro- phosphite | Fluoro- phosphite | Hydrogen- Phosphonate/ Other |
| 0.25 | 0.7 | 0 | 97.7 | 0.96 |
| 2.0 | 1.1 | 0 | 96.5 | 0.82 |

Excluding solvent, acid, and salts, the final product contained 96.5% fluorophosphite.

EXAMPLE 4

A glass reaction vessel was charged with 6.5 grams (0.112 moles) of KF, 50 milliliters of toluene, and 6.1 grams (0.102 moles) of acetic acid. The mixture was vigorously stirred under a dry nitrogen atmosphere and slowly heated. At 80° C., 49.5 grams (0.102 moles) of the 2,2'-ethylidenebis(4,6-di-tertbutylphenyl) chlorophosphite starting material prepared in Example 1 dissolved in 100 milliliters of hot toluene was added to the reaction vessel over a 40 minute period. After addition the reaction mixture was stirred for 2 hrs at 80° C. and then poured into a stirred solution containing 100 grams of water and 13 grams of sodium bicarbonate at 65° C. The two phases were thoroughly mixed and separated. The organic phase was washed with two 100 gram portions of water and transfered to a second reaction vessel. Approximately 130 grams of toluene/water was removed by distillation. The concentrated solution wa cooled to 100° C. and 42 grams of 2-propanol was added dropwise. The resulting solution was cooled to 2° C. and the precipitated solids were isolated by filtration. The solids were washed with two 25 gram portions of 2-propanol and dried in a vacuum oven at 85° C. for 18 hrs. The yield of fluorophosphite product was 35.2 grams (73.3% of the theoretical yield) and the melting point was 190–195° C. The product was analyzed by gas chromatography (GC area percent). The results are shown below.

| | |
|---|---|
| fluorophosphite | 98.6% |
| hydrogen phosphonate | 1.4% |

EXAMPLE 5

This example shows the lack of catalytic effect when a carboxylic acid promoter is not utilized in the transhalogenation process of the present invention.

A glass reaction vessel was charged with 0.65 grams (11.2 mmoles) of KF and 5 milliliters of toluene. The mixture was vigorously stirred under a dry nitrogen atmosphere and slowly heated. At 80° C., 5.0 grams (10.1 mmoles) of the 2,2'-ethylidenebis(4,6-di-tert-butylphenyl) chlorophosphite starting material prepared in Example 1 dissolved in 20 milliliters of hot toluene was added to the vessel over a 15 minute period. The reaction mixture was analyzed periodically by gas chromatography (GC area percent). The following table shows the compositions excluding solvent, acid, and salts.

| | Composition (GC Area Percent) | | | |
|---|---|---|---|---|
| Reaction Time (hrs) | Bisphenol[1] | Chloro- phosphite[2] | Fluoro- phosphite | Hydrogen- Phosphonate[3]/ Other |
| 0.25 | 0 | 97.52 | 0.37 | 2.11 |
| 1.0 | 0 | 94.50 | 2.6 | 2.90 |
| 2.0 | 0 | 94.07 | 3.12 | 2.81 |
| 4.0 | 0 | 92.72 | 3.81 | 3.47 |

[1] 2,2'-ethylidenebis(4,6-di-tert-butylphenol). (4,6-di-tert-butylphenol).
[2] 2,2'-ethylidenebis(4,6-di-tert-butylphenyl) (4,6-di-tert-butylphenyl) chlorophosphite.
[3] 2,2'-ethylidenebis(4,6-di-tert-butylphenyl) (4,6-di-tert-butylphenyl) hydrogenphosphonate.

After 4 hours, the reaction mixture analyzed 3.81 area percent fluorophosphite showing the lack of catalytic affect due to the absence of the carboxylic acid promoter.

I claim:

1. A process for exchanging a halogen bonded to a phosphorus atom with fluorine said process comprising reacting a phosphorus compound, having 1–2 halogen atoms selected from chlorine, bromine or iodine bonded directly to phosphorus, with a fluoride salt selected from metal fluorides or ammonium fluoride in an inert solvent in the presence of a promoter amount of a carboxylic acid.

2. A process of claim 1 wherein said halogen atom is chlorine.

3. A process of claim 1 wherein said fluoride salt is an alkali metal fluoride.

4. A process of claim 2 wherein said fluoride salt is an alkali metal fluoride.

5. A process of claim 4 wherein said alkali metal fluoride is potassium fluoride.

6. A process of claim 3 wherein said alkali metal fluoride is potassium fluoride.

7. A process of claim 1 wherein said carboxylic acid is a monocarboxylic acid.

8. A process of claim 1 wherein said carboxylic acid is a dicarboxylic acid.

9. A process of claim 1 wherein said carboxylic acid is a tricarboxylic acid.

10. A process of claim 7 wherein said carboxylic acid is acetic acid.

11. A process of claim 10 wherein said halogen atom is chlorine.

12. A process of claim 11 wherein said fluoride salt is an alkali metal fluoride.

13. A process of claim 12 wherein said alkali metal fluoride is potassium fluoride.

14. A process of claim 13 wherein said solvent is an aromatic hydrocarbon having a normal boiling point in the range of 80–176° C.

15. A process of claim 14 whrein said solvent is xylene.

16. A process of claim 1 wherein said phosphorus compound has the structure

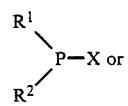 (I)

or

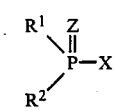 (II)

wherein X is chlorine, bromine or iodine, Z is oxygen or sulphur, $R^1$ is selected from the group consisting of substituted and unsubstituted alkoxy, thioalkoxy, aryloxy, thioaryloxy, cycloalkoxy, alkenoxy, and arylalkoxy and $R^2$ is selected from the same group as $R^1$ or is X, or $R^1$ and $R^2$ can jointly form a substituted or unsubstituted divalent hydrocarbon group bonded at each end through oxygen or sulphur to the phosphorus atom in structures I or II.

17. A process of claim 16 wherein X is chlorine.

18. A process of claim 17 wherein said fluoride salt is an alkali metal fluoride.

19. A process of claim 18 wherein said carboxylic acid is a monocarboxylic acid.

20. A process of claim 19 wherein said alkali metal fluoride is potassium fluoride and said carboxylic acid is a monocarboxylic acid.

21. A process of claim 20 wherein said monocarboxylic acid is acetic acid.

22. A process of claim 20 wherein $R^1$ and $R^2$ jointly form a divalent hydrocarbon group having the structure

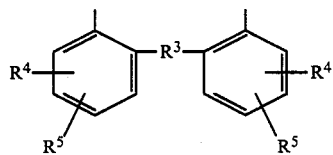

wherein $R^3$ is a methylene or alkylidene bridge or is absent forming a direct ortho-ortho bond between the benzene rings, $R^4$ and $R^5$ are independently selected from alkyl groups, cycloalkyl groups and aralkyl groups and the unsubstituted bond on each benzene ring is bonded through oxygen to said phosphorus atom in structures I or II.

23. A process of claim 21 wherein said hydrocarbon group has the structure

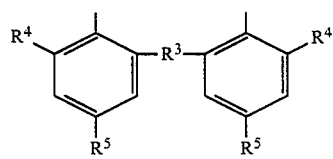

wherein $R^4$ and $R^5$ are alkyl groups.

24. A process of claim 22 wherein $R^4$ and $R^5$ are tertbutyl groups.

25. A process of claim 21 wherein said phosphorus compound has structure I.

26. A process of claim 23 wherein said hydrocarbon group has the structure

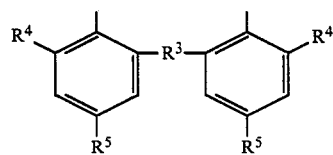

27. A process of claim 24 wherein $R^4$ and $R^5$ are tert-butyl groups.

28. A process of claim 25 wherein $R^3$ is present and is the ethylidene group.

* * * * *